US006713173B2

(12) United States Patent
Mayes et al.

(10) Patent No.: US 6,713,173 B2
(45) Date of Patent: Mar. 30, 2004

(54) MAGNETIZABLE DEVICE

(75) Inventors: Eric Leigh Mayes, Bath (GB); Malvin Nicolas Tyler, Bath (GB)

(73) Assignee: Nanomagnetics Limited, Emersons Greens (GB)

( * ) Notice: Subject to any disclaimer, the term of this patent is extended or adjusted under 35 U.S.C. 154(b) by 0 days.

(21) Appl. No.: 09/730,117

(22) Filed: Dec. 5, 2000

(65) Prior Publication Data

US 2003/0189791 A1 Oct. 9, 2003

Related U.S. Application Data

(63) Continuation of application No. 09/308,166, filed as application No. PCT/GB97/03152 on Nov. 17, 1997.

(30) Foreign Application Priority Data

Nov. 16, 1996 (GB) ................................................ 9623851

(51) Int. Cl.$^7$ .............................................. G11B 5/706

(52) U.S. Cl. ...................... 428/328; 428/329; 428/403; 428/694 BA

(58) Field of Search ................................ 428/328, 329, 428/403, 694 BA, 900

(56) References Cited

U.S. PATENT DOCUMENTS

| | | | |
|---|---|---|---|
| 3,951,904 A | 4/1976 | Tomonaga | 260/40 R |
| 3,966,510 A | 6/1976 | Aonuma et al. | 148/105 |
| 3,975,569 A | * 8/1976 | Sugimatsu et al. | 428/329 |
| 4,009,111 A | 2/1977 | Tamai et al. | 252/62.55 |
| 4,096,040 A | 6/1978 | Grosko | 202/262 |
| 4,214,893 A | * 7/1980 | Tsuganezawa et al. | 428/372 |
| 4,269,826 A | 5/1981 | Zimmermann et al. | 424/101 |
| 4,425,261 A | 1/1984 | Stenius et al. | 502/339 |
| 4,452,773 A | 6/1984 | Molday | 424/1.1 |
| 4,452,896 A | * 6/1984 | Blakemore et al. | 435/252.1 |
| 4,454,234 A | 6/1984 | Czerlinski | 436/526 |
| 4,480,256 A | 10/1984 | Wren | 343/909 |
| 4,533,582 A | * 8/1985 | DePalma et al. | 428/65.3 |
| 4,666,773 A | * 5/1987 | Kitamoto et al. | 428/332 |
| 4,672,040 A | 6/1987 | Josephson | 436/526 |
| 4,735,796 A | 4/1988 | Gordon | 424/9 |
| 4,778,671 A | 10/1988 | Wusirika | 423/592 |
| 4,814,098 A | 3/1989 | Inada et al. | 252/62.51 |
| 4,849,210 A | 7/1989 | Widder | 424/9 |
| 5,043,101 A | 8/1991 | Gordon | 252/408.1 |
| 5,062,991 A | 11/1991 | Siiman et al. | 252/315.2 |
| 5,069,216 A | 12/1991 | Groman et al. | 128/653.4 |
| 5,147,841 A | 9/1992 | Wilcoxon | 502/173 |
| 5,217,804 A | * 6/1993 | James et al. | 428/329 |
| 5,248,589 A | 9/1993 | Bose et al. | 435/2 |
| 5,262,176 A | 11/1993 | Palmacci et al. | 424/9 |
| 5,304,382 A | 4/1994 | Monzyk | 424/489 |
| 5,328,681 A | 7/1994 | Kito et al. | 424/9 |
| 5,338,617 A | 8/1994 | Workinger et al. | 428/551 |
| 5,358,722 A | 10/1994 | Monzyk | 424/489 |
| 5,437,892 A | 8/1995 | Nagayama et al. | 427/123 |
| 5,443,813 A | 8/1995 | Hainfeld | 424/1.17 |
| 5,487,954 A | * 1/1996 | Chin et al. | 428/694 B |
| 5,491,219 A | * 2/1996 | Mann | 530/391.1 |
| 5,505,996 A | 4/1996 | Nagayama | 427/123 |
| 5,512,332 A | 4/1996 | Liberti et al. | 427/550 |
| 5,543,226 A | 8/1996 | Bobrich et al. | 428/423.1 |
| 5,547,748 A | 8/1996 | Ruoff et al. | 428/323 |
| 5,552,072 A | 9/1996 | Arase et al. | 252/62.51 |
| 5,552,229 A | 9/1996 | Brodt et al. | 428/425.9 |
| 5,574,961 A | 11/1996 | Edelstein et al. | 428/548 |
| 5,690,903 A | 11/1997 | Hainfeld | 424/1.49 |
| 5,697,902 A | 12/1997 | Goldenberg | 604/49 |
| 5,766,764 A | 6/1998 | Olli et al. | 428/407 |
| 5,843,569 A | 12/1998 | Kaitsu et al. | 428/323 |
| 5,916,539 A | 6/1999 | Pilgrimm | 424/9.322 |
| 5,965,267 A | * 10/1999 | Nolan et al. | 428/408 |
| 6,054,495 A | 4/2000 | Markowitz et al. | 516/97 |
| 6,103,868 A | 8/2000 | Heath et al. | 528/482 |
| 6,162,532 A | 12/2000 | Black et al. | 428/323 |
| 6,180,389 B1 | 1/2001 | Douglas | 435/235.1 |
| 6,254,662 B1 | 7/2001 | Murray et al. | 75/348 |
| 6,262,129 B1 | 7/2001 | Murray et al. | 516/33 |

FOREIGN PATENT DOCUMENTS

| | | |
|---|---|---|
| DE | 42 44 354 A1 | 7/1993 |
| EP | 0 049 770 | 4/1982 |
| EP | 0 525 199 | 2/1993 |
| EP | 0 686 448 A2 | 12/1995 |
| EP | 0 586 052 B1 | 7/1997 |
| EP | 0884739 A1 | 12/1998 |
| EP | 0 977 182 A2 | 2/2000 |
| EP | 1 186 659 A1 | 3/2002 |
| WO | 8800060 A1 | 1/1988 |
| WO | 89/11154 | 11/1989 |
| WO | 9305818 A1 | 4/1993 |
| WO | 98/29535 | 7/1998 |
| WO | 9946782 A2 | 9/1999 |
| WO | 00/45171 | 8/2000 |
| WO | 00/71169 A2 | 11/2000 |
| WO | 01/74406 A2 | 10/2001 |

OTHER PUBLICATIONS

Dickson et al, Properties of Magnetoferritin: A Novel Biomagnetic Nanoparticle, 3$^{rd}$ International Conference on Nanostructured Materials, Kona HI, Jul. 8–12, 1996, Nanostructured Materials Vol 9 pp. 595–598.*

Meldrum et al, Magnetoferritin: In vitro Synthesis of a Novel Magnetic Protein, Science vol. 257, Jul. 24, 1992.*

Yau et al, Scanning Tunneling Microscopy of Ferritin Nanostructures, Modern Physics Letters B, Vol 9, Nos 3 & 4 (1995) pp187–193.*

(List continued on next page.)

Primary Examiner—Stevan A. Resan
(74) Attorney, Agent, or Firm—Testa, Hurwitz & Thibeault, LLP

(57) ABSTRACT

There is disclosed a magnetic recording medium, which includes a magnetizable layer thereon, wherein said magnetizable layer comprises a plurality of ferri- or ferromagnetic particles each having a largest dimension no greater than 100 nm, and each of which particles represents a separate ferromagnetic domain.

62 Claims, No Drawings

OTHER PUBLICATIONS

Calvert et al, Biomimetic Mineralization in and on Polymers, Chem. Mater. 1996, 8, pp. 1715–1727.*

Hong J. et al., "Granular Magnetic Cobalt Metal/Polymer Thin Film System," IEEE transactions on Magnetics, vol. 32, No. 5, pp. 4475–4477.

Meldrum et al., "Magnetoferritin: In Vitro Synthesis of a Novel Magnetic Protein", Science, vol. 257, Jul. 24, 1992, pp. 522–523.

Huang et al., Construction of a Ferritin Reactor: An Efficient Means for Trapping Various Heavy Metal Ions in Flowing Seawater, Journal of Protein Chemistry, vol. 19, No. 6, 2000.

Kenji et al., "Nanometer–Size Structures Fabricated by Bio–Nano–Process", Abstract, Meiji University.

Li et al., "Growth of Single–Walled Carbon Nanotubes From Discrete Catalytic Nanoparticles of Various Sizes", J. Phys. Chem. B, 105, pp. 11424–11431, 2001

Warne et al., "Self Assembled Nanoparticulate Co : Pt for Data Storage Applications", IEEE Transactions on Magnetics, vol. 36, No. 5, Sep. 2000.

Yamashita, "Fabrication of a Two–Dimensional Array of Nano–Particles Using Ferritin Molecule", Thin Solid Films, 393, pp. 12–18, 2001.

Harris "The Production of Paracrystalline Two–Dimensional Monolayers of Purified Protein Molecules," Micron, Pergamon Press Ltd., United Kingdom, vol. 13, No. 2, pp. 147–168 (1982).

Matsunaga "Synthesis of Nano–Scale Ultrafine Particles Using Biomolecules," Kagaku (Kyoto), vol 46, ISS. 7, p. 498 (1991).

Meldrum et. al. Synthesis of Inorganic Nanophase Materials in Supramolecular Protein Cages, Nature, vol. 349, No. 21 (Feb. 1991).

Ford et al., "Ferritin: Design and Formation of an Iron–Storage Molecule," Phil. Trans. R. Soc. Lond. vol. B304, No. 1121, Feb. 13, 1984, pp. 551–565.

Wardeska et al., "Metal Ion Complexes of Apoferritin," The Journal of Biological Chemistry, vol. 261, No. 15, May 25, 1986, pp. 6677–6683.

Stefanini et al., "On the Mechanism of Horse Spleen Apoferritin Assembly: A Sedimentation Velocity and Circular Dichroism Study," Biochemistry, vol. 26, No. 7, Apr. 7, 1987, pp. 1831–1837.

Price et al., "Binding of Beryllium and Other Divalent Metal Ions," The Journal of Biological Chemistry, vol. 258, No. 18, Sep. 25, 1983, pp. 10873–10880.

Treffry et al., "Spectroscopic Studies on the Binding of Iron, Terbium, and Zinc by Apoferritin," Journal of Inorganic Biochemistry, vol. 21, No. 1 (1984), pp. 9–20.

Bidan et al. "New Nanocomposites Based on Tailor Dressed Magnetic Particles in a Poypyrrole Matrix" Advanced Materials, VCH Verlagsgesellschaft, Weinheim, Germany vol. 6, No. 2, pp. 152–155 (Feb. 1, 1994).

Xu et al. "Collapse of Apo– and Magnetoferritins at the Air–Water Interface," J Colloid Interface Sci, vol. 167, No. 2, pp. 314–319 (1994).

Gider et al. "Classical and Quantum Magnetism in Synthetic Ferritin Proteins" Journal of Applied Physics, American Institute of Physics, New York, vol. 79, No. 8, pp. 5324–5326 (Apr. 15, 1996).

Moskowitz, et al. "Determination of the Preexponential Frequency Factor for Superparamagnetic Maghemite Particles in Magnetoferritin," J. Geophys. Res., Solid Earth, American Geophysical Union, vol. 102, No. B10 (1997).

Meldrum, "Nanoscale Synthesis in Organized Assemblies (Ferritin, Electron Transfer, Magnetotactic Bacteria)," University of Bath (United Kingdom) (1992).

* cited by examiner

MAGNETIZABLE DEVICE

RELATED APPLICATIONS

This application is a continuation of U.S. Ser. No. 09/308,166, filed on Jun. 25, 1999, which is a national stage application of International Application No. PCT/GB97/03152, filed Nov. 17, 1997, which claims priority to Great Britain application No. 9623851.4, filed on Nov. 16, 1996.

This invention relates to a magnetizable device which comprises a magnetic layer composed of domain-separated, nanoscale (e.g. 1–100 nm) ferromagnetic particles. The magnetizable device of the invention may be used as a magnetic storage device having improved data storage characteristics. In particular, the invention relates to magnetic storage media comprising single-domain, domain-separated, uniform, ferromagnetic nanoscale (e.g. 1–100 nm) particles which may be arranged into a regular 2-D packed array useful in the storage of information.

Among the possible pathways to ultrahigh-density ($>=1$ Gbit/in$^2$) magnetic media is the use of nanoscale (1–100 nm) particles. Beyond the standard requirements for magnetic media, a viable particulate media should have a small standard deviation in particle size as well as the particles being exchange decoupled. These requirements are necessary to avoid adverse media noise. Current methods of fabricating nanoscale particles, such as arc-discharge or multiple target ion-beam sputtering, have not fully addressed these two requirements. Moreover, if the uniform particles are arranged into an ordered array, each particle can represent a "bit" of information at a predictable location further increasing the media's efficiency. This invention details methods of producing particulate media that meet these requirements for ultrahigh-density recording. This invention is also an open system which allows for the production of a variety of magnetic materials, such that the media can be tuned for different applications.

In particular this invention details the use of an iron storage protein, ferritin, whose internal cavity is used to produce the nanoscale particles. Ferritin is utilised in iron metabolism throughout living species and its structure is highly conserved among them. It consists of 24 subunits which are arranged to provide a hollow shell roughly 8 nm in diameter. The cavity normally stores 4500 iron(III) atoms in the form of paramagnetic ferrihydrite. However, this ferrihydrite can be removed (a ferritin devoid of ferrihydrite is termed "apoferritin") and other materials may be incorporated. Examples include ceramics, superparamagnetic magnetite, acetaminophen, and even the sweetener aspartame. To address magnetic media concerns, the invention incorporates ferromagnetically ordered materials.

According to a first aspect of the present invention, there is provided a magnetizable device which comprises a magnetic layer composed of domain-separated, ferromagnetic particles each of which has a largest dimension no greater than 100 nm.

According to a second aspect of the invention, there is provided a magnetic recording medium which includes a magnetizable layer, wherein said magnetizable layer comprises a plurality of ferromagnetic particles each having a largest dimension no greater than 100 nm, and each of which particles represents a separate ferromagnetic domain. The magnetizable layer is preferably supported on a nonmagnetic substrate.

According to a third aspect of the present invention, there is provided a magnetic composition comprising a plurality of ferromagnetic particles each of which is bound to an organic macromolecule, and each of which has a largest dimension no greater than 100 nm. In this aspect of the invention, it is preferred that said organic macromolecule is ferritin from which the normal core ferrihydrite has been removed and replaced by a ferromagnetic particle.

As used herein, the term "ferromagnetic" embraces materials which are either "ferromagnetic" and "ferrimagnetic". Such usage is common in the electrical engineering art.

The ferromagnetic particles used in the invention should be of a material and size such that they possess ferromagnetic properties at ambient temperatures (e.g 15° C. to 30° C.).

Preferably, the ferromagnetic particles each have a largest dimension no greater than 50 nm, more preferably less than 25 nm and most preferably smaller than 15 nm. The largest dimension of the ferromagnetic particles should not be so small that the particle will lose its ferromagnetic property and become superparamagnetic at the desired operating temperature of the recording medium. Typically, for operation at ambient temperature, this means that the magnetic particles will normally be no smaller than about 3 nm in their largest diameter.

In the magnetizable device of the first aspect of this invention and the magnetic recording medium of the second aspect of this invention, the distance between adjacent ferromagnetic domains is preferably as small as possible to permit the maximum number of discrete domains in a given area, and provide the maximum storage capacity for the recording medium. The actual lower limit will vary for different materials and other conditions such as the temperature at which the recording medium is to be used. The key requirement, however, is that neighbouring domains should not be able to interfere magnetically with each other to the extent that the magnetic alignment of any domain can be altered by neighbouring domains. Typically, the lower limit on the spacing of the domains is about 2 nm. The distance between adjacent domains will be determined by the density of discrete domains required. Typically, however, to take advantage of the miniaturization possibilities provided by the invention, the distance between adjacent domains will be no greater than 10 nm.

Generally the particles will be uniform in size, by which we mean that the particles do not vary in largest diameter by more than about 5%. One of the advantages of the use in the invention of an organic macromolecule which binds a magnetic particle by surrounding it is that this can be used to select particles of a uniform size.

In the case where the particles are spheroidal, it will be the diameter of the particles which must be no greater than 100 nm.

In preferred embodiments of all aspects of this invention, each ferromagnetic particle is encased, or partially encased, within an organic macromolecule. The term macromolecule means a molecule, or assembly of molecules, and may have a molecular weight of up 500 kD, typically less than 500 kD. Ferritin has a molecular weight of 400 kD.

The macromolecule should be capable of binding by encasing or otherwise organising the magnetic particle, and may therefore comprise a suitable cavity capable of containing the particle; a cavity will normally be fully enclosed within the macromolecule. Alternatively, the macromolecule may include a suitable opening which is not fully surrounded, but which nevertheless is capable of receiving and supporting the magnetic particle; for example, the opening may be that defined by an annulus in the macromolecule. For example, suitable macromolecules which may be used in the invention are proteins, for example the protein apoferritin (which is ferritin in which the cavity is empty), flagellar L-P rings, cyclodextrins, self-assembled cyclic peptides. As an alternative to encasing the magnetic particles within the macromolecule, they may be organised on the macromolecule, such as on a bacterial S-layer.

Other materials which may be used in the invention to organise the ferromagnetic particles are inorganic-silica networks such as MCM type materials, dendrimers and micellar type systems.

The presently preferred macromolecule for use in the invention is the apoferritin protein which has a cavity of the order of 8 nm in diameter. The ferri- or ferromagnetic particles to be accommodated within this protein should have a diameter no greater than 8 nm.

The bound particles of this aspect of the present invention with a coating that inhibits aggregation and oxidation, also helping them to be domain-separated.

In the magnetizable device of the first aspect of this invention and the magnetic recording medium of the second aspect of this invention, the particles are preferably arranged in a 2-D ordered array which would yield an ultrahigh-density magnetic media.

The ferromagnetic material may be a metal, such as cobalt, iron, or nickel; a metal alloy, such as an alloy which contains aluminium, barium, bismuth, cerium, chromium, cobalt, copper, iron, manganese, molybdenum, neodymium, nickel, niobium, platinum, praseodymium, samarium, strontium, titanium, vanadium, ytterbium, yttrium or a mixture thereof; a metal ferrite such as a ferrite containing barium, cobalt, or strontium; or an organic ferromagnetic material.

When generating nanoscale particles, one major concern is that the particles produced are not superparamagnetic. Superparamagnetic particles are those which have permanent magnetic dipole moments, but the moments' orientations with respect to the crystallographic axes fluctuate with time. This is not useful for a practical magnetic storage media. Superparamagnetism depends on the volume, temperature, and anisotropy of the particles. Via energy considerations, one can derive an equation relating these quantities. The volume at which a particle becomes superparamagnetic ($V_p$) is given by: $V_p = 25$ kT/K, where k is Boltzman's constant, T the temperature of the particle in degrees Kelvin, and K the anisotropy constant of the material. Using this formula, it is possible to determine the temperature at which a particle becomes superparamagnetic (the "blocking temperature") for a given material at a fixed volume. In our specific case, the fixed volume is 8 nm in ferritin. If a cobalt metal particle with only crystalline anisotropy (that value being $45 \times 10^5$) is a sphere with a diameter of 8 nm, the blocking temperature is 353° K. This is within the range of temperatures experienced within a hard disk drive, and the cobalt particles may prove to be a useful storage medium. Obviously, there are other considerations such as the materials' coercivity, moment, saturation magnetisation, and relaxation time. By tuning the materials incorporated into the ferritin, though, these can be addressed.

Ferritin is utilised in iron metabolism throughout living species and its structure is highly conserved among them. It consists of 24 subunits arranged in a 432 symmetry which provide a hollow shell roughly 8 nm in diameter. The cavity normally stores 4500 iron (III) atoms in the form of paramagnetic ferrihydrite. However, this ferrihydrite can be removed (a ferritin devoid of ferrihydrite is termed "apoferritin") and other materials may be incorporated. The subunits in ferritin pack tightly, however there are channels into the cavity at the 3-fold and 4-fold axes. Lining the 3-fold channels are residues which bind metals such as cadmium, zinc, and calcium. By introducing such divalent ions one can potentially bind ferritin molecules together, or at least encourage their proximal arrangement.

One method of preparing a 2-D packed array of ferromagnetically ordered particles of uniform size up to 8 nm includes the removal of the ferrihydrite core from the native ferritin in aqueous solution, the incorporation of ferromagnetically ordered cobalt metal particles by sodium borohydride reduction of the aqueous Co(II) solution into the ferritin cavities, the generation of a narrow size distribution through ultracentrifugation, the injection of particles into an MES/glucose subphase solution upon which the 2-D array assembles, and the transfer of the 2-D array to a substrate which is then carbon coated. In this method, the ferritin source may be a vertebrate, invertebrate, plant, fungi, yeast, bacteria, or one produced through recombinant techniques.

In the method described, a metal alloy core may be produced by sodium borohydride reduction of a water soluble metal salt. Other oxidation methods include carbon, carbon monoxide, hydrogen, or hydrazine hydrate solution. Alternatively, a suitable solution may be oxidised to yield a metal ferrite core. Oxidation may be chemical or electrochemical to yield the metal ferrite.

In this method, other methods of selecting a narrow size distribution may be employed such as short or long column meniscus depletion methods or magnetic field separation.

Further, in this method, divalent metal salts containing cadmium, calcium, or zinc may be added into the subphase solution to aid in particle ordering.

Further, in this, other methods of arranging the particles into a 2-D array may be employed, such as solution evaporation onto a solid substrate.

Further, in this method, the 2-D array may be coated with carbon-based films such as hydrogenated or nitrogen doped diamond-like carbon, or with silicon-based films such as silicon dioxide.

In the present invention, ferritin may be used to enclose a ferromagnetic particle whose largest dimension is limited by ferritin's inner diameter of 8 nm. The particles are produced first by removing the ferrihydrite core to yield apoferritin. The is done by dialysis against a buffered sodium acetate solution under a nitrogen flow. Reductive chelation using thioglycolic acid is used to remove the ferrihydrite core. This is followed by repeated dialysis against a sodium chloride solution to completely remove the reduced ferrihydrite core from solution. Once the apoferritin is produced, ferri or ferromagnetic particles are incorporated in the following ways. The first is by reducing a metal salt solution in the presence of apoferritin. This is performed in an inert atmosphere to protect the metal particles from oxidation which would lessen their magnetic benefit. A combination of metal salts in solution can also be reduced to generate alloys or alloy precursors. Sintering or annealing in a magnetic field may be necessary to generate the useful magnetic alloys. Another method is to oxidise a combination of an iron(II) salt and another metal salt. This gives a metal ferrite particle which does not suffer negatively from oxidation. The metal salts which are beneficial include salts of aluminium, barium, bismuth, cerium, chromium, cobalt, copper, iron, manganese, molybdenum, neodymium, nickel, niobium, platinum, praseodymium, samarium, strontium, titanium, vanadium, ytterbium, and yttrium.

A narrow size distribution of particles is necessary to avoid media noise. Such a distribution can be obtained through a variety of procedures including, but not limited to, density gradient centrifugation or magnetic field separation.

While the production procedure detailed uses native horse spleen ferritin, this invention should not be seen as limited to that source. Ferritin can be found in vertebrates, invertebrates, plants, fungi, yeasts, bacteria, or even produced through recombinant techniques. By creating mutant apoferritins lacking the divalent binding site, others have found that the mutant proteins assemble into oblique assemblies as opposed to the regular hexagonal close-packed.

While ferritin seems to be an ideal system for generating nanoscale particles, it is not the only system available. For example, flagellar L-P rings are tubular proteins with an inner diameter of 13 nm. By creating a 2-D array of these proteins, metal films could be deposited into the tubular centres to create perpendicular rods of magnetic material. Also metal reduction in the presence of a microemulsion can be used to generate nanoscale particles which are coated with surfactant. This invention is open to other nanoscale particle production methods.

Finally an ordered arrangement of the particles is desired. One way to accomplish this is by injecting an aqueous solution of particles into an MES/glucose subphase solution contained in a Teflon trough. The particles spread at the air-subphase interface, and a portion denature to form a monolayer film. The 2-D arrangement of encased particles occurs underneath this monolayer. After 10 minutes at room temperature, the arrangement and monolayer are transferred to a substrate by placing the substrate directly onto the monolayer for 5 minutes. After withdrawing the substrate, the attached arrangement is coated with a thin layer of carbon for protection. Other methods such as solution evaporation onto a solid substrate can also give 2-D arrangements, and this invention should not be seen as limited in its arrangement methods.

EXAMPLE 1

This example illustrates the preparation of apoferritin from horse spleen ferritin. Apoferritin was prepared from cadmium-free native horse spleen ferritin (CalBiochem, 100 mg/ml) by dialysis (molecular weight cut-off of 10–14 kDaltons) against sodium acetate solution (0.2 M) buffered at pH 5.5 under a nitrogen flow with reductive chelation using thioglycolic acid (0.3 M) to remove the ferrihydrite core. This is followed by repeated dialysis against sodium chloride solution (0.15 M) to completely remove the reduced ferrihydrite core from solution.

EXAMPLE 2

This example illustrates the preparation of cobalt metal within apoferritin. The apoprotein is added to a deaerated TES/sodium chloride solution (0.1/0.4 M) buffered at pH 7.5 to give an approximate 1 mg/ml working solution of the protein. A deaerated cobalt(II) [for example, as the acetate salt] solution (1 mg/ml) was added incrementally such that the total number of atoms added was approximately 500 atoms/apoprotein molecule. This was allowed to stir at room temperature for one day in an inert atmosphere. This is followed by reduction of the cobalt(II) salt with sodium borohydride to cobalt(0) metal. The final product yielded a solution of cobalt particles, each surrounded by a ferritin shell.

EXAMPLE 3

This example illustrates the preparation of a metal alloy such as yttrium cobalt ($YCo_5$) within apoferritin. The metal alloy follows the same procedure as Example 2 but using a 1:5 ratio of yttrium(III) [for example, as the acetate salt] to cobalt(II) [for example, as the acetate salt]. The final product yielded a solution of yttrium cobalt particles, each surrounded by a ferritin shell.

EXAMPLE 4

This example illustrates the preparation of a metal ferrite such as cobalt ferrite ($CoO.Fe_2O_3$) within apoferritin. The apoprotein is added to a deaerated MES/sodium chloride solution (0.1/0.4 M) buffered at pH 6 to give an approximate 1 mg/ml working solution of the protein. A deaerated solution of cobalt(II) [for example, as the acetate salt] and iron(II) [for example, as the ammonium sulphate salt] in a ratio of 1:2 is added incrementally and allowed to air-oxidise. The final product yielded a solution of cobalt ferrite particles, each surrounded by a ferritin shell.

EXAMPLE 5

This example illustrates the 2-D arrangement of ferritin-encased magnetic particles. An aqueous solution of particles [from Examples 2–4, and whose uniformity in size has been selected] is injected into an MES/glucose subphase solution (0.01 M/2%) contained in a Teflon trough. The particles spread at the air-subphase interface, and a portion denature to form a monolayer film. The 2-D arrangement of encased particles occurs underneath this monolayer. After 10 minutes at room temperature, the arrangement and monolayer are transferred to a substrate by placing the substrate directly onto the monolayer for 5 minutes. After withdrawing the substrate, the attached arrangement is coated with a thin layer of carbon for protection.

What is claimed is:

1. A data storage medium comprising a magnetizable layer, wherein said magnetizable layer comprises a plurality of at least partially encased ferromagnetic particles comprising a metal or metal alloy, wherein each of said ferromagnetic particles has been formed and is at least partially encased within the cavity of one of a protein or protein macromolecule, wherein said cavity of said protein or protein macromolecule is of a uniform predetermined size and shape.

2. The medium according to claim 1, wherein the protein is apoferritin.

3. The data storage medium according to claim 1, wherein the ferromagnetic particles are selected from the group of metals consisting of: cobalt, platinum, iron, and nickel.

4. The data storage medium according to claim 3, wherein the ferromagnetic particles are cobalt metal particles.

5. The data storage medium according to claim 1, wherein the ferromagnetic particles comprise an alloy of two or more metals selected from the group consisting of: aluminium, barium, bismuth, cerium, chromium, cobalt, copper, iron, manganese, molybdenum, neodymium, nickel, niobium, platinum, praseodymium, samarium, strontium, titanium, vanadium, ytterbium, and yttrium.

6. The data storage medium according to claim 5, wherein the ferromagnetic particles are ferromagnetic metal alloy particles selected from the group of metal alloys consisting of: an alloy of cobalt and platinum; an alloy of cobalt, platinum and chromium; an alloy of iron and platinum; an alloy of manganese and aluminum; and alloy of samarium and cobalt; and an alloy of neodymium and iron.

7. A magnetic recording device comprising a magnetic recording medium comprising a magnetizable layer comprising a plurality of at least partially encased ferromagnetic particles comprising a metal or metal alloy, wherein each of said particles has been formed and is at least partially encased within the cavity of one of a protein or protein macromolecule, and wherein said cavity of said protein or protein macromolecule is of a uniform predetermined size and shape.

8. The device according to claim 7, wherein the protein is apoferritin.

9. The magnetic recording device according to claim 7, wherein the ferromagnetic particles are selected from the group of metals consisting of: cobalt, platinum, iron, and nickel.

10. The magnetic recording device according to claim 9, wherein the ferromagnetic particles are cobalt metal particles.

11. The magnetic recording device according to claim 7, wherein the ferromagnetic particles comprise an alloy of two or more metals selected from the group consisting of: aluminium, barium, bismuth, cerium, chromium, cobalt, copper, iron, manganese, molybdenum, neodymium, nickel, niobium, platinum, praseodymium, samarium, strontium, titanium, vanadium, ytterbium, and yttrium.

12. The magnetic recording device according to claim 11, wherein the ferromagnetic particles are ferromagnetic metal alloy particles selected from the group consisting of: an alloy of cobalt and platinum; an alloy of cobalt, platinum and chromium; an alloy of iron and platinum; an alloy of manganese and aluminium; and alloy of samarium and cobalt; and an alloy of neodymium and iron.

13. A method for creating a data storage medium comprising a magnetizable layer, said method comprising the steps of:
    forming a plurality of at least partially encased ferromagnetic particles comprising a metal or metal alloy, each of said plurality of ferromagnetic particles formed and at least partially encased within the cavity of one of a protein or protein macromolecule, wherein said cavity of said protein or protein macromolecule is of a uniform predetermined size and shape; and
    depositing said plurality of ferromagnetic particles on a surface.

14. The method according to claim 13, wherein the protein macromolecule is apoferritin.

15. The method according to claim 13, wherein the ferromagnetic particles are selected from the group of metals consisting of: cobalt, platinum, irons and nickel.

16. The method according to claim 15, wherein the ferromagnetic particles are cobalt metal particles.

17. The method according to claim 13, wherein the ferromagnetic particles comprise an alloy of two or more metals selected from the group consisting of: aluminium, barium, bismuth, cerium, chromium, cobalt, copper, iron, manganese, molybdenum, neodymium, nickel, niobium, platinum, praseodymium, samarium, strontium, titanium, vanadium, ytterbium, and yttrium.

18. The method according to claim 13, wherein the ferromagnetic particles are ferromagnetic metal alloy particles selected from the group consisting of: an alloy of cobalt and platinum; an alloy of cobalt, platinum and chromium; an alloy of iron and platinum; an alloy of manganese and aluminium; and alloy of samarium and cobalt; and an alloy of neodymium and iron.

19. The method according to claim 13, wherein said ferromagnetic particles are formed by reducing a solution containing a metal salt, or a combination of metal salts, in the presence of the protein or protein macromolecule in an inert atmosphere.

20. A method for creating a magnetic recording device comprising the steps of:
    forming a plurality of at least partially encased ferromagnetic particles comprising a metal or metal alloy, each of said plurality of ferromagnetic particles formed and at least partially encased within the cavity of one of a protein or protein macromolecule, wherein said cavity of said protein or protein macromolecule is of a uniform predetermined size and shape; and
    depositing said plurality of ferromagnetic particles on a surface.

21. A data storage medium comprising a magnetizable layer, wherein said magnetizable layer comprises a plurality of at least partially encased ferromagnetizable particles comprising a metal or metal alloy, wherein each of said ferromagnetizable particles has been formed and is at least partially encased within the cavity of one of a protein or protein macromolecule, wherein said cavity of said protein or protein macromolecule is of a uniform predetermined size and shape; and wherein said plurality of ferromagnetizable particles are deposited on a surface.

22. The medium according to claim 21, wherein the protein macromolecute is apoferritin.

23. A magnetic recording device comprising a magnetic recording medium comprising a magnetizable layer comprising a plurality of at least partially encased ferromagnetizable particles comprising a metal or metal alloy, wherein each of said ferromagnetizable particles has been formed and is at least partially encased within the cavity of one of a protein or protein macromolecule, wherein said cavity of said protein or protein macromolecule is of a uniform predetermined size and shape; and wherein said plurality of ferromagnetizable particles are deposited on a surface.

24. The device according to claim 23, wherein the protein macromolecule is apoferritin.

25. A method for creating a data storage medium comprising a magnetizable layer, said method comprising the steps of:
    forming a plurality of at least partially encased ferromagnetizable particles comprising a metal or metal alloy, each ferromagnetizable particle formed and at least partially encased within the cavity of one of a protein or protein macromolecule, and wherein said cavity of said protein or protein macromolecule is of a uniform predetermined size and shape, and
    depositing said plurality of ferromagnetizable particles on a surface.

26. The method of claim 25 wherein the ferromagnetizable particles comprise an alloy of two or more metals selected from the group consisting of: aluminium, barium, bismuth, cerium, chromium, cobalt, copper, iron, manganese, molybdenum, neodymium, nickel, niobium, platinum, praseodymium, samarium, strontium, titanium, vanadium, ytterbium, and yttrium.

27. The method of claim 25 wherein the ferromagnetizable particles are ferromagnetizable metal alloy particles selected from the group consisting of: an alloy of cobalt and platinum; an alloy of cobalt, platinum and chromium; an alloy of iron and platinum; an alloy of manganese and aluminum; and alloy of samarium and cobalt; and an alloy of neodymium and iron.

28. The method of claim 25 wherein the protein macromolecule is apoferritin.

29. The method according to claim 25, wherein the ferromagnetizable particles are selected from the group of metals consisting of: cobalt, platinum, iron and nickel.

30. The method of claim 25 wherein the ferromagnetizable particles are cobalt metal particles.

31. The method of claim 25 wherein the ferromagnetizable particles are formed by reducing a solution containing a metal salt, or a combination of metal salts, in the presence of the protein or protein macromolecule in an inert atmosphere.

32. A method for creating a magnetic recording device, said method comprising the steps of:
   forming a plurality of at least partially encased ferromagnetizable particles comprising a metal or metal alloy, each ferromagnetizable particle formed and at least partially encased within the cavity of one of a protein or protein macromolecule, and wherein said cavity of said protein or protein macromolecule is of a uniform predetermined size and shape, and
   depositing said plurality of ferromagnetizable particles on a surface.

33. The method of claim 32 wherein the ferromagnetizable particles comprise an alloy of two or more metals selected from the group consisting of: aluminium, barium, bismuth, cerium, chromium, cobalt, copper, iron, manganese, molybdenum, neodymium, nickel, niobium, platinum, praseodymium, samarium, strontium, titanium, vanadium, ytterbium, and yttrium.

34. The method of claim 32 wherein the ferromagnetizable particles are ferromagnetizable metal alloy particles selected from the group consisting of: an alloy of cobalt and platinum; an alloy of cobalt, platinum and chromium; an alloy of iron and platinum; an alloy of manganese and aluminium; and alloy of samarium and cobalt; and an alloy of neodymium and iron.

35. The method of claim 32 wherein the protein macromolecule is apoferritin.

36. The method according to claim 32, wherein the ferromagnetizable particles are selected from the group of metals consisting of: cobalt, platinum, iron, and nickel.

37. The method of claim 32 wherein the ferromagnetizable particles are cobalt metal particles.

38. The method of claim 32 wherein ferromagnetizable particles are formed by reducing a solution containing a metal salt, or a combination of metal salts, in the presence of the protein or protein macromolecule in an inert atmosphere.

39. A data storage medium comprising a magnetizable layer, wherein said magnetizable layer comprises a plurality of at least partially encased ferromagnetic particles comprising a metal or metal alloy wherein each of said particles has been formed and is at least partially encased within the cavity of one of a protein or protein macromolecule, and wherein said cavity of said protein or protein macromolecule is of a uniform predetermined size and shape and said particles having been annealed.

40. The medium according to claim 39, wherein the protein macromolecule is apoferritin.

41. The medium of claim 39 wherein the ferromagnetic particles comprise an alloy of two or more metals selected from the group consisting of: aluminium, barium, bismuth, cerium, chromium, cobalt, copper, iron, manganese, molybdenum, neodymium, nickel, niobium, platinum, praseodymium, samarium, strontium, titanium, vanadium, ytterbium, and yttrium.

42. The medium of claim 39 wherein the ferromagnetic particles are ferromagnetic metal alloy particles selected from the group consisting of: an alloy of cobalt and platinum; an alloy of cobalt, platinum and chromium; an alloy of iron and platinum; an alloy of manganese and aluminium; and alloy of samarium and cobalt; and an alloy of neodymium and iron.

43. The medium of claim 39, wherein the ferromagnetic particles are selected from the group of metals consisting of: cobalt, platinum, iron, and nickel.

44. The medium of claim 39 wherein the ferromagnetic particles are cobalt metal particles.

45. A magnetic recording device comprising a magnetic recording medium comprising a magnetizable layer comprising a plurality of at least partially encased ferromagnetic particles comprising a metal or metal alloy wherein each of said particles has been formed and is at least partially encased within the cavity of one of a protein or protein macromolecule, and wherein said cavity of said protein or protein macromolecule is of a uniform predetermined size and shape and said particles having been annealed.

46. The device according to claim 45 wherein the protein macromolecule is apoferritin.

47. The device of claim 45 wherein the ferromagnetic particles comprise an alloy of two or more metals selected from the group consisting of: aluminium, barium, bismuth, cerium, chromium, cobalt, copper, iron, manganese, molybdenum, neodymium, nickel, niobium, platinum, praseodymium, samarium, strontium, titanium, vanadium, ytterbium, and yttrium.

48. The device of claim 45 wherein the ferromagnetic particles are ferromagnetic metal alloy particles selected from the group consisting of: an alloy of cobalt and platinum; an alloy of cobalt, platinum and chromium; an alloy of iron and platinum; an alloy of manganese and aluminum; and alloy of samarium and cobalt; and an alloy of neodymium and iron.

49. The device of claim 45 wherein the ferromagnetic particles are selected from the group of metals consisting of: cobalt, platinum, iron and nickel.

50. The device of claim 45 wherein the ferromagnetic particles are cobalt metal particles.

51. A method for creating a data storage medium comprising a magnetizable layer, said method comprising the steps of:
   forming a plurality of at least partially encased ferromagnetizable particles comprising a metal or metal alloy, each ferromagnetizable particle formed and at least partially encased within the cavity of one of a protein or protein macromolecule, and wherein said cavity of said protein or protein macromolecule is of a uniform predetermined size and shape,
   depositing said plurality of ferromagnetizable particles on a surface, and
   annealing said ferromagnetizable particles.

52. The method according to claim 51 wherein the protein macromolecule is apoferritin.

53. The method of claim 51 wherein the ferromagnetizable particles comprise an alloy of two or more metals selected from the group consisting of: aluminium, barium, bismuth, cerium, chromium, cobalt, copper, iron, manganese, molybdenum, neodymium, nickel, niobium, platinum, praseodymium, samarium, strontium, titanium, vanadium, ytterbium, and yttrium.

54. The method of claim 51 wherein the ferromagnetizable particles are ferromagnetizable metal alloy particles selected from the group consisting of: an alloy of cobalt and platinum; an alloy of cobalt, platinum and chromium; an alloy of iron and platinum; an alloy of manganese and aluminum; and alloy of samarium and cobalt; and an alloy of neodymium and iron.

55. The method of claim 51 wherein the ferromagnetizable particles are selected from the group of metals consisting of: cobalt, platinum, iron, and nickel.

56. The method of claim 51 wherein the ferromagnetizable particles are cobalt metal particles.

57. A method for creating a magnetic recording device, the method comprising the steps of:

forming a plurality of at least partially encased ferromagnetizable particles comprising a metal or metal alloy, each ferromagnetizable particle formed and at least partially encased within the cavity of one of a protein or protein macromolecule, and wherein said cavity of said protein or protein macromolecule is of a uniform predetermined size and shape, depositing said plurality of ferromagnetizable particles on a surface, and annealing said particles.

58. The method according to claim 57 wherein the protein macromolecule is apoferritin.

59. The method of claim 57 wherein the ferromagnetizable particles comprise an alloy of two or more metals selected from the group consisting of: aluminum, barium, bismuth, cerium, chromium, cobalt, copper, iron, manganese, molybdenum, neodymium, nickel, niobium, platinum, praseodymium, samarium, strontium, titanium, vanadium, ytterbium, and yttrium.

60. The method of claim 57 wherein the ferromagnetizable particles are ferromagnetizable metal alloy particles selected from the group of consisting of: an alloy of cobalt and platinum; an alloy of cobalt, platinum and chromium; an alloy of iron and platinum; an alloy of manganese and aluminum; and alloy of samarium and cobalt; and an alloy of neodymium and iron.

61. The method of claim 57 wherein the ferromagnetizable particles are selected from the group of metals consisting of: cobalt, platinum, iron, and nickel.

62. The method of claim 57 wherein the ferromagnetizable particles are cobalt metal particles.

* * * * *